United States Patent
Yang et al.

(10) Patent No.: US 11,304,012 B1
(45) Date of Patent: Apr. 12, 2022

(54) EQUALIZER ADJUSTMENT METHOD AND ELECTRONIC DEVICE

(71) Applicant: PixArt Imaging Inc., Hsin-Chu County (TW)

(72) Inventors: Kuo-Ping Yang, Taipei (TW); Neo Bob Chih-Yung Young, Taipei (TW); Wei-Ren Lan, Taipei (TW)

(73) Assignee: PIXART IMAGING INC., Hsin-Chu County (TW)

( * ) Notice: Subject to any disclaimer, the term of this patent is extended or adjusted under 35 U.S.C. 154(b) by 0 days.

(21) Appl. No.: 17/158,043

(22) Filed: Jan. 26, 2021

(30) Foreign Application Priority Data

Sep. 24, 2020 (CN) .......................... 202011018739.7

(51) Int. Cl.
*H04R 25/00* (2006.01)
*A61B 5/00* (2006.01)
*A61B 5/12* (2006.01)

(52) U.S. Cl.
CPC ........... *H04R 25/505* (2013.01); *A61B 5/123* (2013.01); *A61B 5/7435* (2013.01); *A61B 5/7475* (2013.01); *H04R 25/558* (2013.01); *H04R 25/70* (2013.01); *H04R 2225/55* (2013.01)

(58) Field of Classification Search
CPC .... H04R 25/00; H04R 25/554; H04R 25/505; A61B 5/04; A61B 5/123; A61B 2503/12; A61B 5/121; A61B 5/1176; A61N 1/36032; H04N 5/57; H04N 5/60
See application file for complete search history.

(56) References Cited

U.S. PATENT DOCUMENTS

| 8,634,701 B2 * | 1/2014 | Kang ................. G06K 9/00315 386/248 |
| 2020/0169688 A1 * | 5/2020 | Miyasaka .......... H04N 21/4852 |

* cited by examiner

*Primary Examiner* — Amir H Etesam
(74) *Attorney, Agent, or Firm* — Bacon & Thomas, PLLC

(57) ABSTRACT

An equalizer adjustment method applied to an electronic device is disclosed. The equalizer adjustment method includes: storing an age gain value list in the storage module, wherein the age gain value list includes a plurality of age sections, each age section respectively includes a set of correction parameters, and the set of correction parameters includes a plurality of compensation gain values respectively corresponding to a plurality of target frequencies; via the hearing test module, providing a hearing test; obtaining a hearing test result of a user; via the age determination module and according to the hearing test result, obtaining the age section corresponding to the user; obtaining the set of correction parameters corresponding to the age section corresponding to the user; via the equalizer adjustment module and according to the set of correction parameters, adjusting gain value settings of the equalizer at different target frequencies.

10 Claims, 3 Drawing Sheets

EQUALIZER ADJUSTMENT METHOD AND ELECTRONIC DEVICE

BACKGROUND OF THE INVENTION

1. Field of the Invention

The present invention relates to an equalizer adjustment method and an electronic device; more particularly, the present invention relates to an equalizer adjustment method and an electronic device for measuring the hearing loss of the user accurately so as to adjust the equalizer correspondingly.

2. Description of the Related Art

The equalizer is a tool for adjusting a sound, and the equalizer can adjust the gain value of each of the frequency bands of a sound; that is, the equalizer can adjust the gain value of the sound (or the audio file) at different frequencies to change the auditory effect produced by the output sound. For example, the auditory effect of a blasting sound presented with heavy bass is more shocking and realistic. Therefore, the current equalizer is mainly used for adjusting the output sound. Most existing computers have applications with an equalizer for adjusting the output sound while the user listens to music.

To adjust the gain value settings of the equalizer, the user adjusts the gain values of different frequencies respectively, or the equalizer has many built-in modes such that the user can directly choose different modes to adjust the gain values of multiple frequencies simultaneously while listening to music. However, the hearing abilities of different users are different at different frequencies, and there is still no mode to adjust the gain value based on the actual hearing ability of each user.

Therefore, there is a need to provide a new electronic device and equalizer adjustment method to solve the problem of the prior art.

SUMMARY OF THE INVENTION

The object of the present invention is to provide an equalizer adjustment method for measuring the hearing loss of the user accurately so as to adjust the equalizer correspondingly.

To achieve the abovementioned object, an equalizer adjustment method of the present invention is applied to an electronic device. The electronic device includes a sound processing device. The sound processing device includes an equalizer, a hearing test module, an age determination module, an equalizer adjustment module and a storage module. The equalizer, the hearing test module, the age determination module, the equalizer adjustment module and the storage module are electrically connected to one another. The equalizer adjustment method includes: storing an age gain value list in the storage module, wherein the age gain value list includes a plurality of age sections, each of the plurality of age sections respectively includes a set of correction parameters, and the set of correction parameters includes a plurality of compensation gain values respectively corresponding to a plurality of target frequencies; via the hearing test module, providing a hearing test; obtaining a hearing test result of a user; via the age determination module and according to the hearing test result, obtaining the age section corresponding to the user; obtaining the set of correction parameters corresponding to the age section corresponding to the user; via the equalizer adjustment module, according to the set of correction parameters, adjusting a gain value setting of the equalizer at different target frequencies.

According to one embodiment of the present invention, the hearing test provides a frequency-converted sound; a frequency of the frequency-converted sound rises or falls over time.

According to one embodiment of the present invention, the electronic device further includes a screen and an order receiving module; the hearing test further provides a testing interface which is displayed on the screen, the testing interface provides a confirmation button for the user to operate when hearing or not hearing the frequency-converted sound, and the order receiving module receives the hearing test result.

According to one embodiment of the present invention, the electronic device further includes a sound playing module, the equalizer adjustment method further including: via the equalizer, adjusting a sound according to the set of correction parameters, and playing the sound via the sound playing module.

According to one embodiment of the present invention, the plurality of compensation gain values are between 1.5 and 15; when the plurality of target frequencies are between 250 Hz and 2000 Hz, the plurality of compensation gain values corresponding to the plurality of target frequencies are between 1.5 and 4; when the plurality of target frequencies are more than 4000 Hz, the plurality of compensation gain values are between 1.7 and 12.

Another object of the present invention is to provide an electronic device for measuring the hearing loss of the user accurately so as to adjust the equalizer correspondingly.

To achieve the abovementioned object, an electronic device of the present invention includes an equalizer, a hearing test module, an age determination module, an equalizer adjustment module and a storage module. The storage module is used for storing an age gain value list, wherein the age gain value list includes a plurality of age sections, each of the plurality of age sections respectively includes a set of correction parameters, and the set of correction parameters includes a plurality of compensation gain values respectively corresponding to a plurality of target frequencies. The hearing test module is used for providing a hearing test to obtain a hearing test result of a user. The age determination module is used for obtaining one of the plurality of age sections corresponding to the user according to the hearing test result. The equalizer adjustment module is electrically connected to the equalizer, the storage module, the hearing test module and the age determination module, and equalizer adjustment module is used for obtaining the set of correction parameters corresponding to the one of the plurality of age sections according to the one of the plurality of age sections and also for adjusting a gain value setting of the equalizer at different frequencies according to the set of correction parameters.

According to one embodiment of the present invention, the hearing test module further includes a frequency-converted sound provider, and the frequency-converted sound provider is used for providing a frequency-converted sound when executing the hearing test; a frequency of the frequency-converted sound rises or falls over time.

According to one embodiment of the present invention, the electronic device further includes a screen and an order receiving module; the hearing test module further includes a testing interface provider, the testing interface provider is used for providing a testing interface which is displayed on the screen when executing the hearing test, and the testing interface provides a confirmation button for the user to operate when hearing or not hearing the frequency-converted sound, and the order receiving module receives the hearing test result.

According to one embodiment of the present invention, the electronic device further includes a sound playing module; the equalizer is used for adjusting a sound according to the set of correction parameters, and the sound playing module plays the sound.

DETAILED DESCRIPTION OF THE PREFERRED EMBODIMENT

Figure 1:
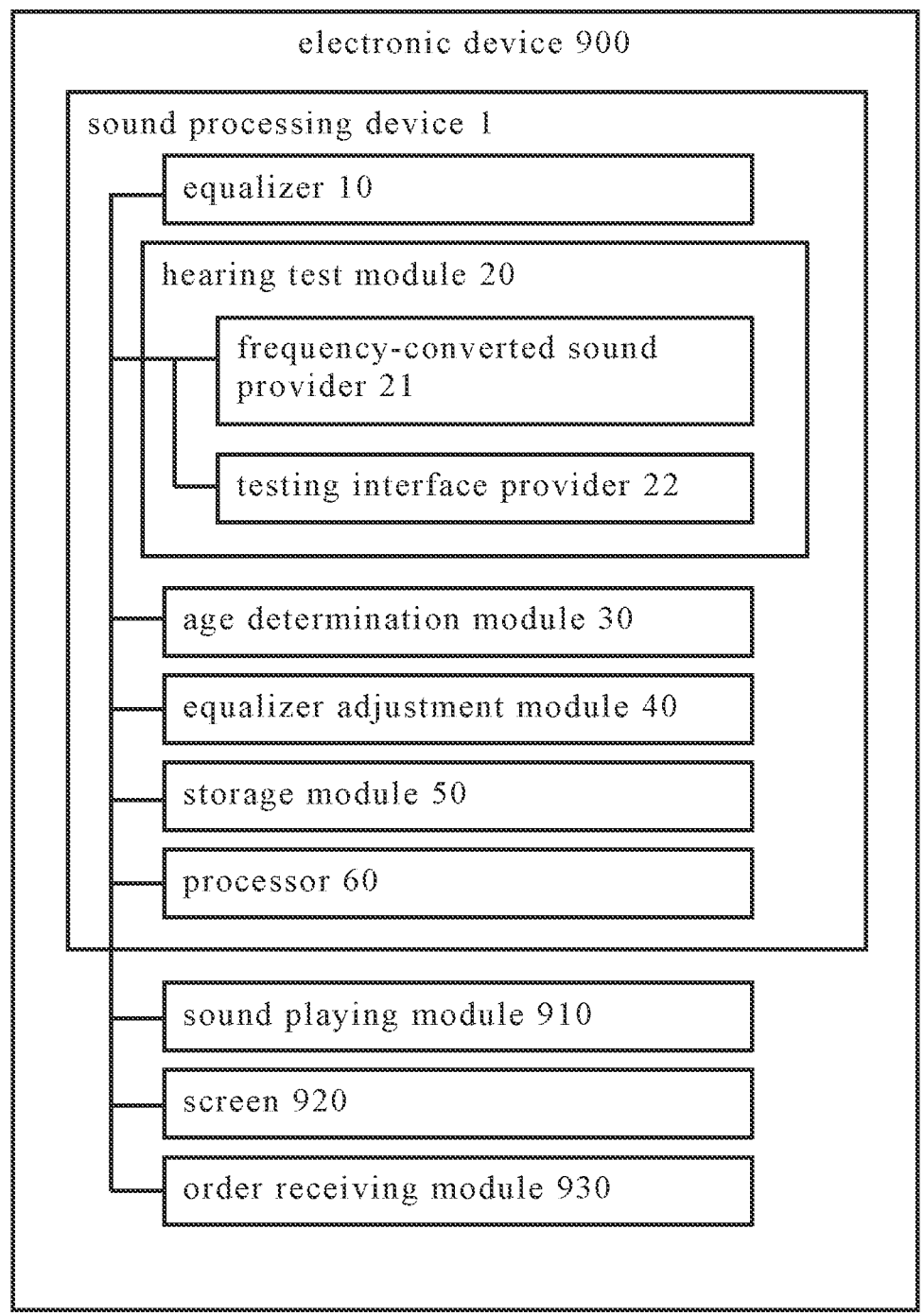
FIG. 1 illustrates a system structure drawing of the electronic device in one embodiment of the present invention.
Figure 2:
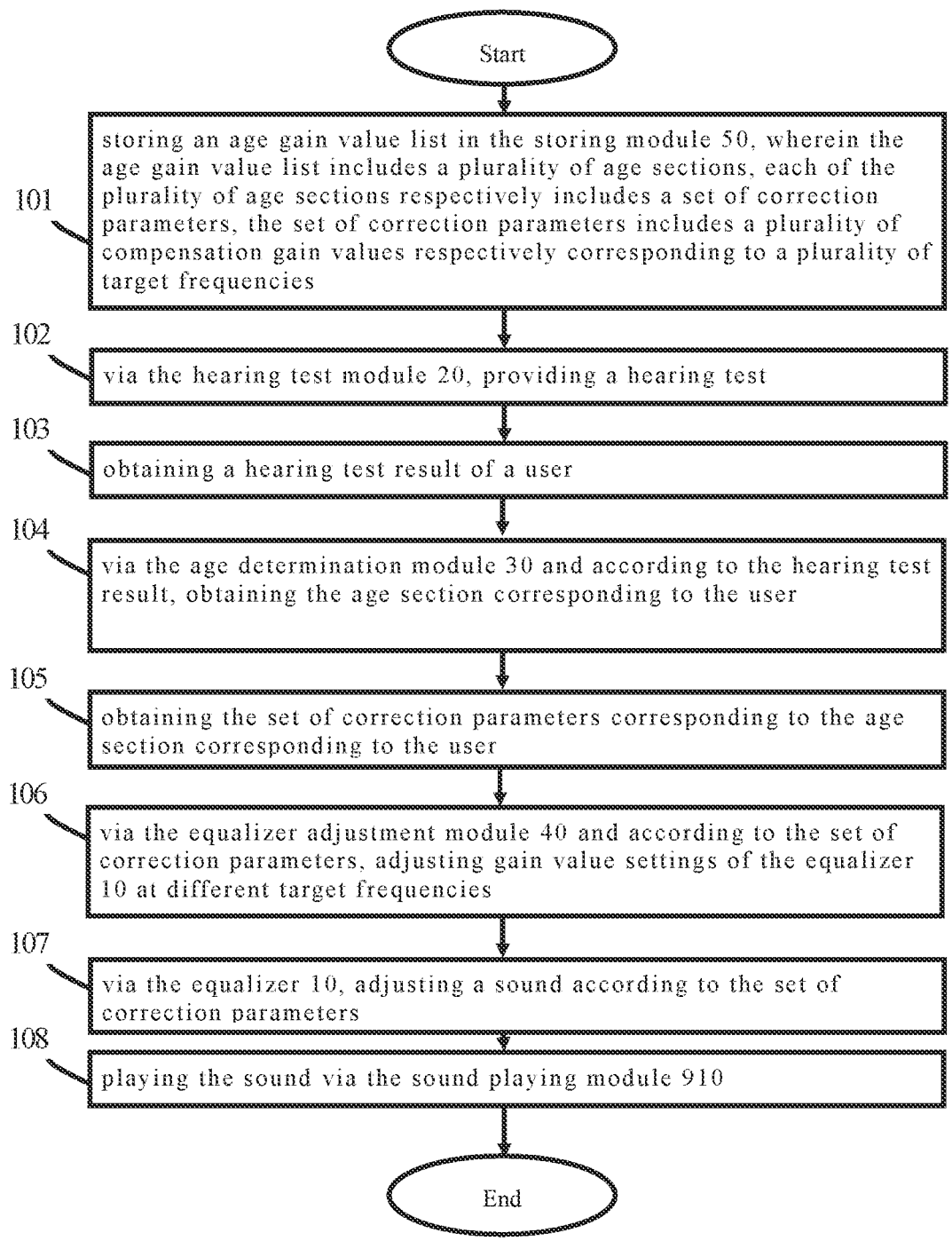
FIG. 2 illustrates a step flowchart of the equalizer adjustment method in one embodiment of the present invention.
Figure 3:
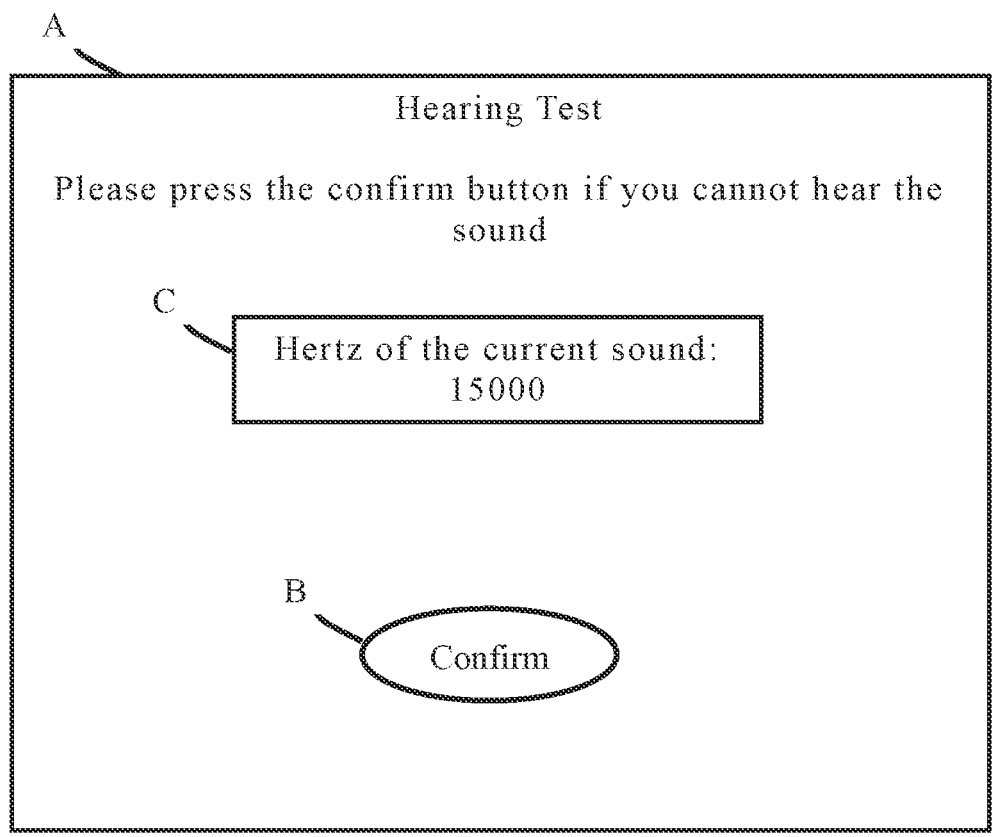
FIG. 3 illustrates a schematic drawing of the testing interface in one embodiment of the present invention.

Please refer to FIG. 1 to FIG. 3 about the equalizer adjustment method and the electronic device in one embodiment of the present invention. FIG. 1 illustrates a system structure drawing of the electronic device in one embodiment of the present invention. FIG. 2 illustrates a step flowchart of the equalizer adjustment method in one embodiment of the present invention. FIG. 3 illustrates a schematic drawing of the testing interface in one embodiment of the present invention.

As shown in FIG. 1, in one embodiment of the present invention, the equalizer adjustment method and the electronic device 900 for executing the method can measure the hearing loss of the user accurately so as to adjust the equalizer correspondingly. The electronic device 900 is a cellphone, but the type of the electronic device 900 is not limited to the abovementioned description, for the electronic device 900 can also be another device with a calculation processing and sound playing function, such as a notebook computer or a tablet computer. The electronic device 900 includes a sound playing module 910, a screen 920, an order receiving module 930 and a sound processing device 1. The sound playing module 910 is a speaker for playing sound. The screen 920 is used for displaying the picture for the user to view. The order receiving module 930 is provided for the user to operate to receive the order given by the user. The order receiving module 930 is a touch module integrated with the screen 920, a keyboard or a mouse.

In one embodiment of the present invention, the sound processing device 1 can measure the hearing loss of the user accurately so as to adjust the equalizer correspondingly, allowing the equalizer to accurately adjust the sound according to the hearing loss to be suitable for the user. The sound processing device 1 is electrically connected to the sound playing module 910, the screen 920 and the order receiving module 930. The sound processing device 1 includes an equalizer 10, a hearing test module 20, an age determination module 30, an equalizer adjustment module 40, a storage module 50 and a processor 60. The equalizer 10 can adjust the gain value of the sound at different frequencies according to the correction parameter obtained by the equalizer adjustment method; for example, if the gain value of 500 Hz (specific frequency) is set to increase by 5 dB, the volume of the sound output by the equalizer 10 at 500 Hz will increase by 5 dB. Because the equalizer 10 is a common sound outputting adjustment tool, the structure and theory of the equalizer 10 are already disclosed in the prior art, so there is no need for further description.

In one embodiment of the present invention, the storage module 50 is a memory for storing an age gain value list, and the age gain value list includes a plurality of age sections, which are the first age section to the Nth age section. The age ranges represented by the first age section to the Nth age section gradually increase. Each of the plurality of age sections respectively includes a set of correction parameters, the set of correction parameters includes a plurality of compensation gain values respectively corresponding to the plurality of target frequencies, and the plurality of compensation gain values of the same target frequency increase as the value of N increases to compensate for the hearing loss of an older user such that the sound can be adjusted correspondingly. The age gain value list also lists the average highest frequency which can be heard easily by users in each of the plurality of age sections. The age gain value list is shown below.

| Highest audible frequency | age | Hz | | | | | | | |
| --- | --- | --- | --- | --- | --- | --- | --- | --- | --- |
| | | 250 | 500 | 1K | 2K | 4K | 8K | 12.5K | 16K |
| 18000 | 5-29 | 1.9 | 1.9 | 1.7 | 1.5 | 1.7 | 2.5 | 3.7 | 6.5 |
| 16000 | 30-39 | 2.1 | 2.0 | 1.9 | 1.7 | 2.2 | 2.6 | 4.0 | 7.6 |
| 14000 | 40-49 | 2.4 | 2.2 | 2.0 | 1.9 | 2.4 | 2.8 | 5.5 | 9.5 |
| 12000 | 50-59 | 2.4 | 2.4 | 2.4 | 2.1 | 2.7 | 4.2 | 8.3 | 10.4 |
| 10000 | 60-69 | 2.6 | 2.6 | 2.5 | 2.8 | 4.0 | 6.3 | 10.1 | 11.8 |
| 8000 | 70-90 | 3.0 | 3.1 | 3.2 | 4.0 | 5.6 | 8.8 | 11.4 | 12.0 |

The age gain value list includes the age section of 5-29 years old to the age section of 70-90 years old, and each age section and the frequencies of 250 Hz, 500 Hz, 1 KHz, 2 KHz, 4 KHz, 8 KHz, 12.5 KHz, and 16 KHz have corresponding compensation gain values. As shown in the age gain value list, the compensation gain values are between 1.5 and 15. When the target frequencies are between 250 Hz and 2 KHz, the compensation gain values corresponding to the target frequencies are between 1.5 and 4. If the target frequencies are more than 4 KHz, the compensation gain values are between 1.7 and 12. It is to be known that the compensation gain values of the abovementioned age gain value list are only examples, the number range of the compensation gain values is not limited to the abovementioned design, the age range of the age section is not limited to the abovementioned design, and the age range of the age section can be changed according to the design requirement; for example, the age ranges can be changed to divide the age sections into spans of five years.

As shown in FIG. 1 and FIG. 3, in one embodiment of the present invention, the hearing test module 20 is used for providing a hearing test to obtain a hearing test result of a user. The hearing test module 20 includes a frequency-converted sound provider 21 and a testing interface provider 22. The frequency-converted sound provider 21 is used for providing a frequency-converted sound when executing the hearing test. A frequency of the frequency-converted sound rises or falls over time; for example, the frequency gradually increases from 20 Hz to 20000 Hz or gradually decreases from 20000 Hz to 20 Hz. The testing interface provider 22 is used for providing a testing interface A which is displayed on the screen 920 when executing the hearing test; the testing interface A provides a confirmation button B and a frequency-converted sound information bar C. The testing interface A is provided for the user to operate the confirmation button B to generate the hearing test result when not hearing the frequency-converted sound such that the order receiving module 930 can receive the hearing test result. The frequency-converted sound information bar C can display the current frequency of the frequency-converted sound so that the user can understand the sound range that the user cannot hear and the degree of hearing loss of the user. However, the testing interface A can also be designed for allowing the user to operate the confirmation button B to generate the hearing test result when hearing the frequency-converted sound so that the user can understand the critical value of the audible sound frequency of the user.

In one embodiment of the present invention, the age determination module 30 is a chip with the age determining function for obtaining the age section corresponding to the user according to the hearing test result received in the hearing test.

In one embodiment of the present invention, the equalizer adjustment module 40 is a controlling chip with a parameter adjustment function for obtaining the set of correction parameters corresponding to the age section corresponding to the user, and for adjusting a gain value setting of the equalizer 10 at different frequencies according to the set of correction parameters.

In one embodiment of the present invention, the processor 60 is a central processing unit (CPU) chip, which is electrically connected to the equalizer 10, the storage module 50, the hearing test module 20, the age determination module 30 and the equalizer adjustment module 40, for controlling and coordinating the equalizer 10, the storage module 50, the hearing test module 20, the age determination module 30 and the equalizer adjustment module 40 to work smoothly.

As shown in FIG. 1 to FIG. 3, in one embodiment of the present invention, the equalizer adjustment method is programmed as a software program and stored in the storage module 50. When executing the equalizer adjustment method of the present invention, the electronic device 900 executes Step 101: storing an age gain value list in the storage module 50, wherein the age gain value list includes a plurality of age sections, each of the plurality of age sections respectively includes a set of correction parameters, and the set of correction parameters includes a plurality of compensation gain values respectively corresponding to a plurality of target frequencies.

First, the age gain value list is stored in a storage module 50, and the age gain value list includes a plurality of age sections, which are the first age section to the Nth age section, and the age ranges represented by the first age section to the Nth age section gradually increase. Each of the plurality of age sections respectively includes a set of correction parameters, the set of correction parameters includes a plurality of compensation gain values respectively corresponding to the plurality of target frequencies, and the plurality of compensation gain values of the same target frequency increase as the value of N increases to compensate for the hearing loss of an older user and adjust the sound correspondingly. The age gain value list also lists the average highest frequency which can be heard easily for each of the plurality of age sections.

Then, when the user wants to adjust the settings of the equalizer, the user can operate the electronic device 900 to execute Step 102: via the hearing test module 20, providing a hearing test.

The user can use the electronic device 900 to control the hearing test module 20 to provide a hearing test. The testing interface provider 22 provides a testing interface A on the screen 920, and the frequency-converted sound provider 21 provides a frequency-converted sound which is played by the sound playing module 910 for the user to hear. The frequency of the frequency-converted sound of this embodiment gradually increases over time; thus, the user can press the confirmation button B on the testing interface A when not hearing the frequency-converted sound (for example, when not hearing the sound of 15000 Hz) to generate the hearing test result of "hearing loss above 15000 Hz". However, the hearing test can be designed to change the frequency-converted sound over time such that the frequency gradually decreases from 20000 Hz, and the testing interface A displays the direction "If you hear a sound, please press the confirmation button"; thus, when the user hears the frequency-converted sound and presses the confirmation button, the critical frequency value between normal hearing and the hearing loss of the user can be confirmed.

Then the method executes Step 103: obtaining a hearing test result of a user.

After the user presses the confirmation button B to generate the hearing test result of "hearing loss above 15000 Hz", the hearing test result will be sent to the order receiving module 930, and the order receiving module 930 will send the hearing test result to the processor 60.

Then the method executes Step 104: via the age determination module 30, according to the hearing test result, obtaining the age section corresponding to the user.

The processor 60 sends the hearing test result to the age determination module 30, and the age determination module 30 checks the age gain value list stored in the storage module 50 according to the hearing test result of "hearing loss above 15000 Hz" to obtain the age section corresponding to hearing loss above 15000 Hz, which is the age section of 30-39 years old. After the age determination module 30 obtains the information of the age section of 30-39 years old, the information will be sent to the equalizer adjustment module 40.

Then the method executes Step 105: obtaining the set of correction parameters corresponding to the age section corresponding to the user.

After the equalizer adjustment module 40 receives the information of the age section of 30-39 years old, the equalizer adjustment module 40 will check the age gain value list stored in the storage module 50 and obtain the set of correction parameters corresponding to the age section of 30-39 years old, as shown in the following table.

| Highest audible frequency | | Hz | | | | | | | |
|---|---|---|---|---|---|---|---|---|---|
| | age | 250 | 500 | 1K | 2K | 4K | 8K | 12.5K | 16K |
| 16000 | 30-39 | 2.1 | 2.0 | 1.9 | 1.7 | 2.2 | 2.6 | 4.0 | 7.6 |

Then the method executes Step 106: via the equalizer adjustment module 40, according to the set of correction parameters, adjusting the gain value settings of the equalizer 10 at different target frequencies.

The equalizer adjustment module 40 adjusts the gain value settings of the equalizer 10 at different target frequencies according to the set of correction parameters corresponding to the age section of 30-39 years old.

Then the method executes Step 107: via the equalizer 10, adjusting a sound according to the set of correction parameters.

The equalizer 10 adjusts the sound according to the gain value settings at different target frequencies corresponding to the set of correction parameters corresponding to the age section of 30-39 years old; thus, the sound after adjustment becomes easier to hear for the user with hearing loss corresponding to the age section of 30-39 years old.

Finally, executing Step 108: playing the sound via the sound playing module 910.

The sound adjusted by the equalizer 10 is sent to the sound playing module 910, and the sound playing module 910 plays the sound which is adjusted for the user to hear.

Via the equalizer adjustment method and the electronic device of the present invention, a hearing test is provided to measure the hearing loss of the user accurately and adjust the setting of the equalizer correspondingly; therefore, the sound after adjustment can be coordinated with the hearing loss of the user and become easier to hear for the user with hearing loss.

What is claimed is:

1. An equalizer adjustment method, applied to an electronic device, wherein the electronic device comprises a sound processing device, the sound processing device comprises an equalizer, a hearing test module, an age determination module, an equalizer adjustment module and a storage module, wherein the equalizer, the hearing test module, the age determination module, the equalizer adjustment module and the storage module are electrically connected to one another, the equalizer adjustment method comprising:

storing an age gain value list in the storage module, wherein the age gain value list comprises a plurality of age sections, each of the plurality of age sections respectively comprises a set of correction parameters, and the set of correction parameters comprises a plurality of compensation gain values respectively corresponding to a plurality of target frequencies;

via the hearing test module, providing a hearing test;

obtaining a hearing test result of a user;

via the age determination module and according to the hearing test result, obtaining an age section corresponding to the user;

obtaining the set of correction parameters corresponding to the age section corresponding to the user; and via the equalizer adjustment module, according to the set of correction parameters, adjusting a gain value setting of the equalizer at different target frequencies.

2. The equalizer adjustment method as claimed in claim 1, wherein the hearing test provides a frequency-converted sound; a frequency of the frequency-converted sound rises or falls over time.

3. The equalizer adjustment method as claimed in claim 2, wherein the electronic device further comprises a screen and an order receiving module; the hearing test further provides a testing interface which is displayed on the screen, the testing interface provides a confirmation button for the user to operate when hearing or not hearing the frequency-converted sound, and the order receiving module receives the hearing test result.

4. The equalizer adjustment method as claimed in claim 3, wherein the electronic device further comprises a sound playing module, the equalizer adjustment method further comprising:

via the equalizer, adjusting a sound according to the set of correction parameters; and playing the sound via the sound playing module.

5. The equalizer adjustment method as claimed in claim 4, wherein the plurality of compensation gain values are between 1.5 and 15; when the plurality of target frequencies are between 250 Hz and 2000 Hz, the plurality of compensation gain values corresponding to the plurality of target frequencies are between 1.5 and 4; when the plurality of target frequencies are more than 4000 Hz, the plurality of compensation gain values are between 1.7 and 12.

6. An electronic device, comprising:

an equalizer;

a storage module, for storing an age gain value list, wherein the age gain value list comprises a plurality of age sections, each of the plurality of age sections respectively comprises a set of correction parameters, and the set of correction parameters comprises a plurality of compensation gain values respectively corresponding to a plurality of target frequencies;

a hearing test module, for providing a hearing test to obtain a hearing test result of a user;

an age determination module, for obtaining one of the plurality of age sections corresponding to the user according to the hearing test result; and an equalizer adjustment module, electrically connected to the equalizer, the storage module, the hearing test module and the age determination module, for obtaining the set of correction parameters corresponding to the one of the plurality of age sections according to the one of the plurality of age sections, and for adjusting a gain value setting of the equalizer at different frequencies according to the set of correction parameters.

7. The electronic device as claimed in claim 6, wherein the hearing test module further comprises a frequency-converted sound provider, and the frequency-converted sound provider is used for providing a frequency-converted sound when executing the hearing test; a frequency of the frequency-converted sound rises or falls over time.

8. The electronic device as claimed in claim 7, wherein the electronic device further comprises a screen and an order receiving module; the hearing test module further comprises a testing interface provider, the testing interface provider is used for providing a testing interface which is displayed on the screen when executing the hearing test, and the testing interface provides a confirmation button for the user to operate when hearing or not hearing the frequency-converted sound, and the order receiving module receives the hearing test result.

9. The electronic device as claimed in claim 8, wherein the electronic device further comprises a sound playing module; the equalizer is used for adjusting a sound according to the set of correction parameters, and the sound playing module plays the sound.

10. The electronic device as claimed in claim 9, wherein the plurality of compensation gain values are between 1.5 and 15; when the plurality of target frequencies are between 250 Hz and 2000 Hz, the plurality of compensation gain values corresponding to the plurality of target frequencies are between 1.5 and 4; when the plurality of target frequencies are more than 4000 Hz, the plurality of compensation gain values are between 1.7 and 12.

* * * * *